United States Patent [19]

Plummer

[11] Patent Number: 4,668,792

[45] Date of Patent: * May 26, 1987

[54] INTERMEDIATES TO INSECTICIDAL [1,1'-BIPHENYL]-3-YLMETHYL ESTERS

[75] Inventor: Ernest L. Plummer, Yardley, Pa.

[73] Assignee: FMC Corporation, Philadelphia, Pa.

[*] Notice: The portion of the term of this patent subsequent to May 11, 1999 has been disclaimed.

[21] Appl. No.: 563,711

[22] Filed: Dec. 20, 1983

Related U.S. Application Data

[60] Continuation-in-part of Ser. No. 376,442, May 10, 1982, abandoned, which is a division of Ser. No. 265,940, May 21, 1981, Pat. No. 4,402,973, which is a continuation-in-part of Ser. No. 193,056, Oct. 2, 1980, Pat. No. 4,329,518, which is a continuation-in-part of Ser. No. 076,636, Sep. 18, 1979, abandoned, which is a division of Ser. No. 966,405, Dec. 4, 1978, Pat. No. 4,214,004.

[51] Int. Cl.$^4$ ............... C07D 213/20; C07C 143/68; C07C 143/79

[52] U.S. Cl. ..................... 546/343; 558/44; 558/53; 558/58; 558/54; 534/558; 564/82; 564/282; 564/289; 546/346; 546/347; 560/255; 570/129; 570/185; 568/642; 568/643; 568/807

[58] Field of Search ........... 260/456 R, 456 P; 570/129, 185; 560/255; 568/807, 642, 643; 534/558; 564/82, 83, 87, 92, 282, 289; 546/343, 346, 347; 558/44, 53, 54, 58

[56] References Cited

U.S. PATENT DOCUMENTS

| | | | |
|---|---|---|---|
| 3,850,977 | 11/1974 | Itaya et al. ............ | 260/456 P |
| 4,130,657 | 12/1978 | Plummer .............. | 424/305 |
| 4,214,004 | 7/1980 | Plummer .............. | 424/305 |
| 4,329,518 | 5/1982 | Plummer .............. | 568/807 |
| 4,402,973 | 9/1983 | Plummer .............. | 424/305 |
| 4,434,182 | 2/1984 | Cruickshank et al. ... | 514/640 |
| 4,473,709 | 9/1984 | Montgomery et al. ... | 564/282 |

OTHER PUBLICATIONS

Andersen and Uh, *Synthetic Comm.*, 2, 297 (1972).
Cotton and Stokely, *Chem. Abstr.*, 72, 60177; (1970).
Dauphin and Kergomard, *Bull. Soc. Chim. Fr.*, 486 (1961).
Katritzky, et al., *J. Chem. Soc. Perkin Trans. II*, 45 (1983).
Katritzky and Leahy, *J. Chem. Research (S)*, 28 (1985).
Perrin, "Dissociation Constants of Organic Bases in Aqueous Solution," Butterworths, London 1965, pp. 1, 2, 15 and 74.
Baker, et al., *J. Chem. Soc. (C)*, 1605-1606 (1969).
Beard, et al., *J. Org. Chem.*, 38, 3673-3677 (1973).
Brasen and Hauser, *Org. Syn. Coll.* vol. IV, 582-584 (1963).
Collins, et al., *Tet. Letters*, 3363-3366 (1968).
Crossland, et al., *J. Am. Chem. Soc.*, 93, 4217-4219 (1971).
DeChristopher, et al., *J. Am. Chem. Soc.*, 91, 2384-2385 (1969).
Finch and Schlittler, *Tetrahedron*, 24, 5421-5424 (1968).
Gruntz, et al., *J.C.S. Chem. Comm.*, 701 (1977).
Hartman and Rahrs, *Org. Syn. Coll.* vol. III, 650-652 (1955).
Kirmse, *Angew. Chem. Int. Ed. Engl.*, 15, 251-261 (1976).
March, "Advanced Organic Chemistry," McGraw-Hill, 1977, pp. 322 et seq., 327, 328.
March, *Loc. Cit.*, pp. 227-230.
Meyer, et al., *Chem. Ber.*, 103, 37-45 (1970).
Morrison and Boyd, "Organic Chemistry," 2nd Ed., Allyn and Bacon, Inc, Boston, 1971, pp. 916-918.
Overberger and Anselme, *J. Am. Chem. Soc.*, 86, 658-660 (1964).
Sheehan and Bolhofer, *J. Am. Chem. Soc.*, 72, 2786-2788 (1950).
Subramanian, et al., *Synthesis*, 293-294 (1973).
Szeja, *Synthesis*, 822-823 (1979).
Williams and Halpern, *Synthesis*, 727-728 (1974).
Winberg and Fawcett, *Org. Syn. Coll.* vol. V., 883-886 (1973).
Babavan et al., Chem. Abstract, 84, 58806t (1976).
Gould, "Mechanism and Structure in Organic Chemistry", Holt, Rinehart & Winston, New York, 1959, pp. 258-263.

*Primary Examiner*—Nicky Chan
*Attorney, Agent, or Firm*—H. Robinson Ertelt; R. L. Hansen

[57] ABSTRACT

Substituted [1,1'-biphenyl]-3-ylmethyl compounds carrying leaving groups are intermediates to insecticidal esters.

27 Claims, No Drawings

INTERMEDIATES TO INSECTICIDAL [1,1'-BIPHENYL]-3-YLMETHYL ESTERS

This application is a continuation in part of application Ser. No. 376,442, filed May 10, 1982, now abandoned, which is a division of application Ser. No. 265,940, filed May 21, 1981, now U.S. Pat. No. 4,402,973, which is a continuation in part of application Ser. No. 193,056, filed Oct. 2, 1980, now U.S. Pat. No. 4,329,518, which is a continuation in part of application Ser. No. 076,636, filed Sept. 18, 1979, now abandoned, which is a division of application Ser. No. 966,405, filed Dec. 4, 1978, now U.S. Pat. No. 4,214,004.

This invention pertains to the field of carboxylic acid esters which are pyrethroid insectides, more specifically to processes and intermediates to the insecticidal esters.

Pyrethrins have long been of interest as insecticides. Ever since it was discovered that pyrethrins are organic esters, various synthetic modifications have been made in the carboxylic acid and in the alcohol moieties on either side of the ester linkage. Many of the synthetic pyrethroids are more effective than the natural pyrethrins, and recent modifications have overcome a chronic pyrethrin problem—instability to air and light.

The carboxylic acid moiety in the aforesaid esters is often a 2,2-dimethylcyclopropane-1-carboxylic acid with various substituents in the 3-position. Many variations in the alcohol moiety of the aforesaid esters have been disclosed also, and it has now been found that insecticidal and acaricidal esters result when a substituted [1,1'-biphenyl]-3-ylmethyl alcohol moiety is coupled with certain carboxylic acid moieties as disclosed in U.S. Pat. Nos. 4,402,973 and 4,214,004.

The pyrethroid esters are prepared by reaction between a carbonyl halide, e.g., a chloride RCOCl, wherein R is a suitable acid moiety, e.g., as described in U.S. Pat. No. 4,402,973; an acid, RCOOH; an ester, RCOOR', wherein R' is conveniently a $C_1$–$C_6$ alkyl group; an anhydride, RCOOR'', wherein R'' is $C_1$–$C_6$ alkylcarbonyl or aryl sulfonyl; or a nitrile, RCN, and an appropriate substituted [1,1'-biphenyl]-3-ylmethanol. Substituted [1,1'-biphenyl]-3-ylmethanols are disclosed and claimed in U.S. Pat. No. 4,329,518.

Alternatively, the esters are prepared by classical nucleophilic substitution, i.e., by reacting an acid or acid salt, RCOOM, wherein R is as defined above, and M is an alkali or alkaline earth metal, e.g., Li, Na, K, Ca, or Mg; a transition metal, e.g., Ag; or ammonium, or alkyl-substituted ammonium, with a substituted [1,1'-biphenyl]-3-ylmethyl compound wherein the benzylic carbon atom carries a "leaving group" which is readily displaced by carboxylate anions. Substituted [1,1'-biphenyl]-3-ylmethyl compounds carrying such leaving groups are the subject of this application.

The substituted [1,1'-biphenyl]-3-ylmethyl compounds within the scope of this application are described by the structural formula

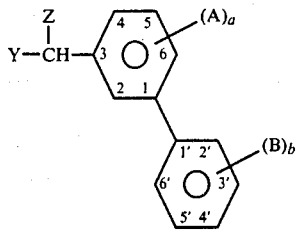

wherein
Y is a leaving group readily displaced by pyrethroid carboxylate anions, Z is hydrogen, or Z is an electron pair when Y is a diazo group, and
(1) b is 0, a is 1–4, and
when a is 1,
A is 2- or 6-halo, 4-chloro, 4-fluoro, 5-fluoro, 2-lower alkyl, or 2-trifluoromethyl, and
when a is 2,
A is fluoro, 2- and 4-substituents independently selected from fluoro, chloro, bromo, and lower alkyl, with the proviso that only one may be bromo or alkyl other than methyl , or 2- and 6-substituents independently selected from fluoro, chloro and methyl, and
when a is 3 or 4,
A is fluoro, or may be as when a is 1 or a is 2 with one or two additional fluoro groups;
or
(2) a is 0, b is 1–5, and
when b is 1,
B is halo, 2'- or 3'-lower alkyl, 2'- or 3'-trifluoromethyl, or 2'- or 3'-lower alkoxy, and
when b is 2,
B is fluoro, or 2'- and 4'-substituents independently selected from fluoro, chloro and bromo, and
when b is 3, 4 or 5,
B is fluoro;
or
(3) a is 1–4, b is 1–4, and
A is fluoro or a 2-substituent selected from chloro, bromo, and lower alkyl with 0 to 3 fluoro groups, and B is fluoro or a 2'-substituent selected from chloro and methyl with 0 to 3 fluoro groups.

In the aforesaid description the term "lower" modifying alkyl or alkoxy means a linear or branched chain of 1–6, preferably 1–4, carbon atoms. The term "halo" employed alone or modifying alkyl means fluorine, chlorine or bromine.

Especially useful are those compounds in which halo is restricted to fluoro and chloro, and lower alkyl is restricted to methyl, especially where a is not greater than 3 and b is not greater than 2. Methyl, ethyl, and methoxy, ethoxy are preferred lower alkyl and lower alkoxy substituents, respectively.

Those compounds wherein a is 0 are desirable, especially those containing a single substituent, B, at the 2'-position, most especially fluoro or methyl. When more than one substituent B is present, they are preferably halo, especially fluoro. Among those compounds wherein b is 0, it is preferred that A be fluoro or chloro, especially fluoro. When the compound has 2-substitution, it is preferred that it also be substituted at the 4-position when A is halo or lower alkyl. 2-Methyl[1,1'-biphenyl]-3-ylmethyl and 2,4-dimethyl[1,1'-biphenyl]-3- ylmethyl compounds are attractive, pyrethroid esters prepared therefrom being especially active.

The substituted [1,1'-biphenyl]-3-ylmethyl alcohols or bromides are obtained by one or more of several different methods, depending on the specific compounds desired. These methods are described in U.S. Pat. No. 4,329,518, which description is incorporated herein by reference. A [1,1'-biphenyl]-3-ylmethyl alcohol, prepared by one of those methods, can be converted into the corresponding substituted [1,1'-biphenyl]-3-ylmethyl bromide by treating a solution of the alcohol in ether with phosphorous tribromide or phosphorus pentabromide. Similarly, a substituted [1,1-biphenyl]-3-ylmethyl bromide can be converted into the corresponding alcohol by first treating the bromide with sodium acetate in acetic acid and then treating the thus produced biphenyl acetate with sodium hydroxide in methanol. These techniques are available in the prior art.

Suitable leaving groups Y in the aforesaid structural formula are known in the art today and include bromo, chloro, (methylsulfonyl)oxy, and (4-methylbenzenesulfonyl)oxy, which are disclosed in U.S. Pat. No. 4,329,518. It is expected that additional leaving groups readily displaced by carboxylate anions will be discovered in the future. The instant invention contemplates these future developments. It is recognized that any leaving groups readily displaced by carboxylate anions are and will be functional equivalents for Y in the aforesaid structural formula for the substituted [1,1'-biphenyl]-3-ylmethyl compounds of this invention.

In order that a leaving group Y will be readily displaced by a carboxylate anion, the anion of the leaving group should be a poorer nucleophile, generally a weaker base, than the carboxylate anion. The relationship between nucleophilicity and basicity is set forth in March, "Advanced Organic Chemistry," McGraw-Hill, 1977, p. 322 et seq. In other words, to a reasonable approximation, the conjugate acid of the leaving group anion should have a $pK_a$ which is less than that of the conjugate carboxylic acid. The $pK_a$'s for a large number of acids are known; e.g., see March, loc. cit., pp. 227–230, and the $pK_a$'s of the conjugate acids of leaving group anions which are now or later become candidates for Y in the aforesaid structural formula can be measured by methods known to those skilled in the art. In general, a substituted [1,1'-biphenyl]-3-ylmethyl compound carrying a desired leaving group can be prepared by nucleophilic displacement on the corresponding compound carrying a leaving group whose anion is a weaker base that the anion of the desired leaving group.

Suitable leaving groups Y include halo, especially chloro and bromo. Preparation of substituted [1,1'-biphenyl]-3-ylmethyl compounds carrying halo leaving groups is disclosed in U.S. Pat. No. 4,329,518. In general, a substituted [1,1'biphenyl]-3-ylmethyl chloride is prepared by chlorination of the corresponding 3-methyl compound with N-chlorosuccinimide, with thionyl chloride, chlorine under irradiation, or with sulfonyl chloride and a peroxide such as benzoyl peroxide, or by treating the corresponding substituted [1,1'-biphenyl]-3-ylmethanol with thionyl chloride. Reaction of substituted [1,1'-biphenyl]-3-ylmethyl compounds carrying halo leaving groups with suitable carboxylates to produce insecticidal esters is described in U.S. Pat. No. 4,214,004 and more generally by Hartman and Rahrs, Org. Syn., Coll. Vol. III, pp. 650–652 (1955), as well as by Finch and Schlittler, Tetrahedron, 24, 5421–5424 (1968). Specific substituted [1,1'-biphenyl]-3-ylmethyl compounds in which Y is halo include, for example, 3-chloromethyl-2,4-dimethyl[1,1'-biphenyl] and 3-bromomethyl-2,4,6-trifluoro[1,1'-biphenyl].

Sulfonyloxy constitutes another suitable type of leaving group Y, e.g., aromatic sulfonyloxy groups of the formula

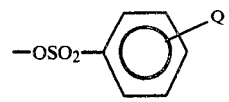

in which the specific ring position substituted by Q and the identity of Q are selected to optimize the $pK_a$ of the conjugate sulfonic acid of the formula

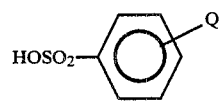

according to the principles described above. Specific leaving groups within this structural representation include those in which Q is selected from hydrogen, lower alkyl (straight or branched chain), lower alkyl substituted with one or more halogen atoms, halogen, or nitro. More specifically, examples include (benzenesulfonyl)oxy; (methylbenzenesulfonyl)oxy, especially (4-methylbenzenesulfonyl)oxy; (bromobenzenesulfonyl)oxy, especially (4-bromobenzenesulfonyl)oxy; and (nitrobenzenesulfonyl)oxy, especially (4-nitrobenzenesulfonyl)oxy. Preparation of substituted [1,1'-biphenyl]-3-ylmethyl compounds having the (4-methylbenzenesulfonyl)oxy leaving group is described in U.S. Pat. No. 4,329,518 and can be accomplished by treating the corresponding 3-ylmethanols with (4-methyl)benzenesulfonyl chloride. Substituted [1,1'-biphenyl]-3-ylmethyl compounds with other leaving groups of this type can be prepared by the same general method, substituting the appropriate sulfonyl chloride, all as described by Szeja, Synthesis, 822–823 (1979). The procedure described by Baker, et al., J. Chem. Soc. (C), 1605–1606 (1969), can be employed when reacting substituted [1,1'-biphenyl]-3-ylmethyl compounds carrying such sulfonyloxy leaving groups with suitable carboxylates. Specific substituted [1,1'-biphenyl]-3-ylmethyl compounds in which Y is an aromatic sulfonyloxy group include, for example, (2-methyl[1,1'-biphenyl]-3-yl)methyl 4-methylbenzenesulfonate, (2,4-dimethyl[1,1'-biphenyl]-3-yl)methyl 4-bromobenzenesulfonate, (2,4,6-trifluoro[1,1'-biphenyl]-3-yl)methyl 4-chlorobenzenesulfonate.

Closely related alkyl or fluoroalkyl sulfonyloxy substitutents, which are also suitable leaving groups Y, are described by the formula

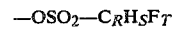

in which R is 1–6, and S+T is 3–13, while S and T are independently 0–13, selected to optimize the $pK_a$ of the conjugate sulfonic acid according to the principles set forth above. Examples of such leaving groups include (alkylsulfonyl)oxy in which T=0, especially lower (alkylsulfonyl)oxy, a specific example being (methanesulfonyl)oxy, in which R=1, S=3 and T=0. Substituted [1,1'-biphenyl]-3-ylmethyl compounds carrying this leaving group are prepared by treating the corresponding 3-ylmethanol with methanesulfonyl chloride as disclosed in U.S. Pat. No. 4,329,518. Substituted [1,1'-biphenyl]-3-ylmethyl compounds with other leaving groups of this type are similarly prepared using the appropriate sulfonyl chloride as described by Meyer, et al., Chem. Ber., 103, 37-45 (1970) and by Szeja, loc. cit. The former reference also describes displacement of the methanesulfonyl group with carboxylate, and that description is applicable to other (alkylsulfonyl)oxy leaving groups as well. Specific substituted [1,1'-biphenyl]-3-ylmethyl compounds in which Y is an (alkylsulfonyl)oxy substituent include, for example, (2-methyl[1,1'-biphenyl]-3-yl)methyl methanesulfonate.

Other useful leaving groups Y of the aforesaid formula are those containing fluorine substituents, i.e., fluoroalkyl. A specific example is the (2,2,2-trifluoroethanesulfonyl)oxy group, with R=2, S=2 and T=3. Substituted [1,1'-biphenyl]-3-ylmethyl compounds carrying the (2,2,2-trifluoroethanesulfonyl)oxy leaving group are prepared from the corresponding 3-ylmethanols by the procedure described by Crossland, et al., J. Am. Chem. Soc., 93, 4217-4219 (1971). Structurally similar are the (trifluoromethanesulfonyl)oxy (R=1, S=0, T=3) and (nonafluorobutylsulfonyl)oxy (R=4, S=0, T=9) leaving groups. Preparation from the corresponding 3-yl-methanols of substituted [1,1'-biphenyl]-3-ylmethyl compounds carrying the former leaving group can be carried out as described by Beard, et al., J. Org. Chem., 38, 3673-3677 (1973), compounds with the latter leaving group by the method of Subramanian, et al., Synthesis, 293-294 (1973). Substituted [1,1'-biphenyl]-3-ylmethyl compounds with other fluoroalkyl sulfonyloxy leaving groups are similarly prepared. Reaction of the fluoroalkyl sulfonyloxy carrying compounds with suitable carboxylates can be effected by the method of Meyer, et al., loc. cit. Specific substituted [1,1'-biphenyl]-3-ylmethyl compounds in which the leaving group Y is fluoroalkylsulfonyl)oxy include, for example, (2,4-dimethyl[1,1'-biphenyl]-3-yl)methyl 2,2,2-trifluoroethanesulfonate and (2,4,6-trifluoro[1,1'-biphenyl]-3-yl)methyl trifluoromethanesulfonate.

Several leaving groups in which nitrogen is bonded to the 3-ylmethyl group are also suitable as Y. Substituted [1,1'-biphenyl]-3-ylmethyl compounds carrying these leaving groups are often obtainable from the corresponding 3-ylmethanamines. The latter can be made from the corresponding 3-ylmethyl bromides by the Grabriel synthesis, the details of which are described by Sheehan and Bolhofer, J. Am. Chem. Soc., 72, 2786-88 (1950) and more generally in Morrison and Boyd, "Organic Chemistry," 2nd Ed., Allyn and Bacon, Inc., Boston, 1971, pp. 916-918. For example, 2-methyl[1,1'-biphenyl]-3-ylmethanamine results as follows, and other substituted [1,1'-biphenyl]-3-ylmethanamines are made similarly.

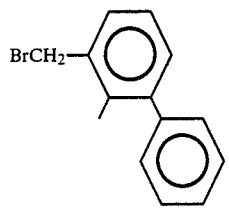

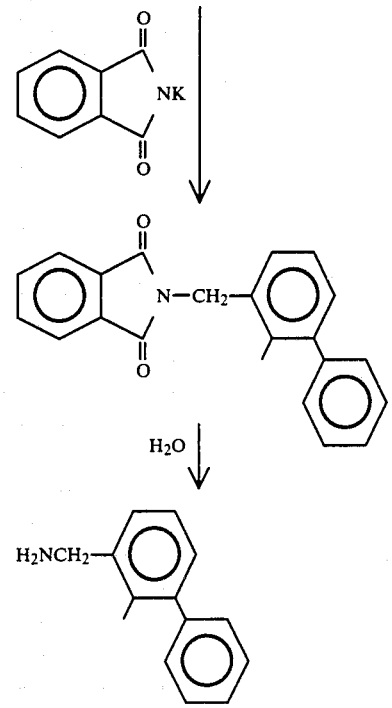

These nitrogen-containing leaving groups include quaternary ammonium of the formula

$-NR_1R_2R_3^+X^-$ in which $R_1$, $R_2$ and $R_3$ are hydrocarbon groups, e.g., independently lower alkyl or phenyl, and $X^-$ is a suitable anion, such as hydroxide, bromide or iodide, all selected to optimize the $pK_a$ of the corresponding conjugate acid as described above. Specific examples include N,N-dimethylbenzenaminium hydroxide and N,N-dimethylmethanaminium bromide. Preparation of substituted [1,1'-biphenyl]-3-ylmethyl compounds with N,N-dimethylbenzenaminium chloride as the leaving group Y from the corresponding 3-ylmethyl chloride, as well as the subsequent reaction thereof with carboxylate can be effected as described by Williams and Halpern, Synthesis, 727-728 (1974). Substituted [1,1'-biphenyl]-3-ylmethyl compounds with N,N-dimethylmethanaminium salts as leaving groups are prepared from the corresponding 3-ylmethyl bromides by the method described by Winberg and Fawcett, Org. Syn., Coll. Vol. V., 883-886 (1973); the displacement with carboxylate can be conducted as described by Brasen and Hauser, Org. Syn., Coll. Vol. IV., 582-584 (1963). Substituted [1,1'-biphenyl]-3-ylmethyl compounds carrying other quaternary ammonium leaving groups are prepared and reacted with suitable carboxylates by similar techniques. Substituted [1,1'-biphenyl]-3-ylmethyl compounds in which the leaving group Y is quaternary ammonium include, for example, N,N,2-trimethyl-N-phenyl[1,1'-biphenyl]-3-ylmethaminium hydroxide and N,N,N,2,4-pentamethyl[1,1'-biphenyl]-3-ylmethaminium bromide.

Additional nitrogen-containing leaving groups suitable as Y are sulfonamido, e.g., aromatic sulfonamido described by the formula

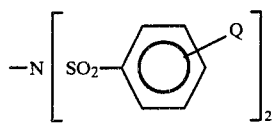

in which the ring position substituted by Q and the specific nature of Q are chosen to optimize the p$K_a$ of the conjugate acid

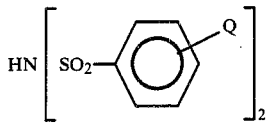

according to the principles set forth above. Specific leaving groups of this type include those in which Q is selected from hydrogen, lower alkyl (straight or branched chain), lower alkyl substituted with one or more halogen atoms, halogen, or nitro. More specifically, examples of such leaving groups include N-(4-methylbenzenesulfonyl)-4-methylbenzenesulfonamido and N-(4-nitrobenzenesulfonyl)-4-nitrobenzenesulfonamido. Preparation of substituted [1,1'-biphenyl]-3-ylmethyl compounds with such leaving groups from the corresponding 3-ylmethanamines may be accomplished by the method of Dechristopher, et al., *J. Am. Chem. Soc.*, 91, 2384–2385 (1969). Reaction of the resultant substituted [1,1'-biphenyl]-3-ylmethyl compounds with suitable carboxylates can be effected by the same method employed for 4-methylbenzenesulfonates, i.e., see Baker, et al. loc. cit. Substituted [1,1'-biphenyl]-3-ylmethyl compounds carrying aromatic sulfonamide leaving groups include, for example, N-(2-methyl[1,1'-biphenyl]-3-yl)methyl-N-(4-methylbenzenesulfonyl)-4-methylbenzenesulfonamide and N-(2,4-dimethyl[1,1'-biphenyl]-3-yl)methyl-N-(4-nitrobenzenesulfonyl)-4-nitrobenzenesulfonamide.

Other useful nitrogen containing leaving groups Y include the pyridinium group, e.g., 1-(2,4,6-triphenylpyridinium),

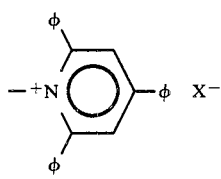

where X$^-$ is an anion such as tetrafluoroborate. Substituted [1,1'-biphenyl]-3-ylmethyl compounds with such leaving groups can be prepared from the corresponding 3-ylmethanamines by the procedure described by Gruntz, et al., *Chem. Commun.*, 701 (1977). The resultant substituted [1,1'-biphenyl]-3-ylmethyl compounds can be reacted with suitable carboxylates by the process described in the same reference. Substituted [1,1'-biphenyl]-3-ylmethyl compounds with pyridinium as the leaving group Y include, for example, 1-(2-methyl[1,1'-biphenyl]-3-yl)methyl-2,4,6-triphenyl-pyridinium tetrafluoroborate.

Diazo is another useful leaving group Y. Substituted [1,1'-biphenyl]-3-ylmethyl compounds carrying diazo as the leaving group can be prepared from the corresponding 3-ylmethanols via the aldehydes using the procedure described by Colins, et al., *Tet. Letters*, 3363–3366 (1968), followed by that of Overberger and Anselme, *J. Am. Chem. Soc.*, 86, 658–660 (1964). For example, (2-methyl[1,1'-biphenyl]-3-yl)diazomethane can be prepared by the following sequence of reactions.

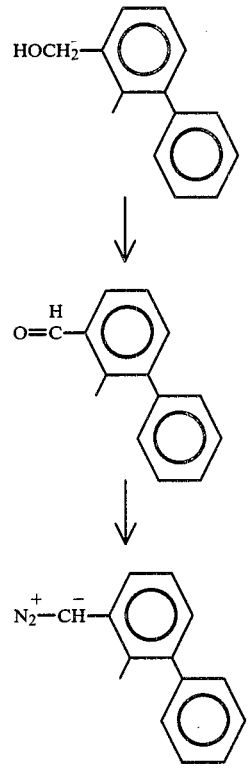

The resultant diazomethane can be reacted with an appropriate carboxylic acid, producing an ester, according to the procedure of Kirmse, *Angew. Chem. Int. Ed. Engl.*, 15, 251–261 (1976).

The invention is not limited to substituted [1,1'-biphenyl]-3-ylmethyl compounds in which the leaving group Y is restricted to the specific substituents recited above. The recitation is by way of exemplification only. Many other functionally suitable substituents are now well known in the art and more are expected to become known in the future, both as to preparing substituted [1,1'-biphenyl]-3-ylmethyl compounds carrying those substituents as well as reacting the resultant substituted [1,1'-biphenyl]-3-ylmethyl compounds in nucleophilic displacement of those substituents with suitable acids or acid salts. As to leaving group Y, this invention contemplates function, rather than specific structure. Guidance in selecting appropriate structure to achieve that function is provided above.

What is claimed is:

1. A subtituted (1,1'-biphenyl)-3-ylmethyl compound of the formula

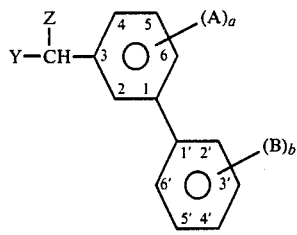

wherein Y is a leaving group readily displaced by pyrethroid carboxylate anions and selected from the group consisting of sulfonyloxy of the formula

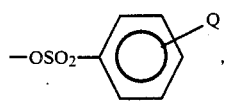

an alkyl or fluoroalkyl sulfonyloxy of the formula $-OSO_2-C_RH_SF_T$ sulfonamido of the formula

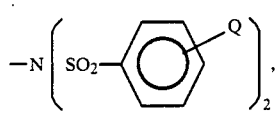

a pyridinium, and diazo, Z is hydrogen, or Z is an electron pair when Y is diazo, Q is selected from hydrogen, lower alkyl (straight or branched chain), lower alkyl substituted with one or more halogen atoms, halogen, and nitro, R is 1-6, S+T is 3-13, and S and T are independently 1-13, and (1) b is 0, a is 1-4, and
when a is 1,
A is 2- or 6-halo, 4-chloro, 4-fluoro, 5-fluoro, 2-lower alkyl, or 2-trifluoromethyl, and
when a is 2,
A is fluoro, 2- and 4-substituents independently selected from fluoro, chloro, bromo, and lower alkyl, with the proviso that only one may be bromo or alkyl other than methyl, or 2- and 6-substituents independently selected from fluoro and chloro, and
when a is 3 or 4,
A is fluoro, or may be as when a is 1 or a is 2 with one or two additional fluoro groups;

or (2) a is 0, b is 1-5, and
when b is 1,
B is halo, 2'- or 3'-trifluoromethyl, or 2'- or 3'-lower alkoxy, and
when b is 2,
B is fluoro, or 2'- and 4'-substituents independently selected from fluoro, chloro and bromo, and
when b is 3, 4 or 5,
B is fluoro;

or (3) a is 1-4, b is 1-4, and
A is fluoro or a 2-substituent selected from chloro, bromo, and lower alkyl with 0 to 3 fluoro groups, and B is fluoro or a 2'-substituent selected from chloro and methyl with 0 to 3 fluoro groups.

2. A substituted (1,1'-biphenyl)-3-ylmethyl compound of claim 1 wherein (1) b is 0, a is 1-4, and
when a is 1,
A is 2-, 4-, or 6-fluoro or chloro, 5-fluoro, or 2-methyl, and
when a is 2,
A is fluoro, 2- and 4-substituents independently selected from fluoro, chloro and methyl, or 2- and 6-substituents independently selected from fluoro and chloro, and
when a is 3 or 4,
A is fluoro, or may be as when a is 1 or a is 2 with one or two additional fluoro groups;

or (2) a is 0, b is 1-5, and
when b is 1,
B is fluoro or chloro, and
when b is 2,
B is fluoro, or 2'- and 4'-substituents independently selected from fluoro and chloro, and
when b is 3, 4 or 5,
B is fluoro;

or (3) a is 1-4, b is 1-4, and
A is fluoro or a 2-substituent selected from chloro and methyl with 0 to 3 fluoro groups, and B is fluoro or a 2'-substituent selected from chloro and methyl with 0 to 3 fluoro groups.

3. A substituted (1,1'-biphenyl)-3-ylmethyl compound of claim 1 wherein (1) b is 0, a is 1-3, and
when a is 1,
A is 2-, 4-, or 6-fluoro or chloro, 5-fluoro, or 2-methyl, and
when a is 2,
A is fluoro, 2- and 4-substituents independently selected from fluoro, chloro and methyl, or 2- and 6-substituents independently selected from fluoro and chloro, and
when a is 3,
A is fluoro, or may be as when a is 1 or a is 2 with one or two additional fluoro groups;

or (2) a is 0, b is 1 or 2, and
when b is 1,
B is fluoro or chloro, and
when b is 2,
B is fluoro, or 2'- and 4'-substituents independently selected from fluoro and chloro;

or (3) a is 1-3, b is 1 or 2, and
A is fluoro or a 2-substituent selected from chloro and methyl with 0 to 2 fluoro groups, and B is fluoro or a 2'-substituent selected from chloro and methyl with 0 or 1 fluoro group.

4. A compound of claim 1 wherein lower alkyl is methyl or ethyl, and lower alkoxy is methoxy or ethoxy.

5. A compound of claim 1 wherein b is 0, a is 1, and A is halo.

6. A compound of claim 1 wherein b is 0, a is 1, and A is 2-methyl.

7. A compound of claim 1 wherein b is 0, a is 2, and A is fluoro, 2- and 4-chloro, 2- and 4-bromo, or 2- and 4-lower alkyl.

8. A compound of claim 7 wherein A is 2- and 4-chloro.

9. A compound of claim 7 wherein A is 2- and 4-fluoro.

10. A compound of claim 7 wherein A is 2- and 4-methyl.

11. A compound of claim 1 wherein b is 0, a is 1-4, and A is fluoro.

12. A compound of claim 11 wherein A is 2-, 4-, 5-, and 6-fluoro.

13. A compound of claim 1 wherein a is 0, b is 1, and B is fluoro, chloro, 3'-trifluoromethyl, or 2'-lower alkoxy.

14. A compound of claim 13 wherein lower alkoxy is methoxy or ethoxy.

15. A compound of claim 13 wherein B is 2'-fluoro.

16. A compound of claim 1 wherein a is 0, b is 2, and B is fluoro or 2'- and 4'-chloro.

17. A compound of claim 1 wherein a is 0, b is 1-5, and B is fluoro.

18. A compound of claim 1 wherein Y is an aromatic sulfonyloxy group of the formula

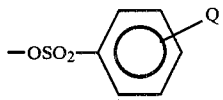

in which Q is selected from hydrogen, lower alkyl (straight or branched chain), lower alkyl substituted with one or more halogen atoms, halogen, or nitro.

19. A compound of claim 18 wherein said aromatic sulfonyloxy group is selected from (benzenesulfonyl)oxy, (methylbenzenesulfonyl)oxy, (bromobenzenesulfonyl)oxy, and (nitrobenzenesulfonyl)oxy.

20. A compound of claim 1 wherein Y is an alkyl or fluoroalkyl sulfonyloxy substituent of the formula

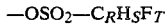

in which R is 1-6, S+T is 3-13, and S and T are independently 0-13.

21. A compound of claim 20 wherein said sulfonyloxy substituent is selected from (methylsulfonyl)oxy, (2,2,2-trifluoroethanesulfonyl)oxy, and (nonafluorobutysulfonyl)oxy.

22. A compound of claim 1 wherein Y is an aromatic sulfonamido group of the formula

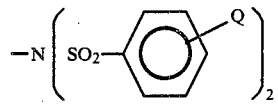

in which Q is selected from hydrogen, lower alkyl (straight or branched chain), lower alkyl substituted with one or more halogen atoms, halogen, and nitro.

23. A compound of claim 22 wherein said sulfonamido group is selected from N-(4-methylbenzenesulfonyl)-4-methylbenzenesulfonamido and N-(4-nitrobenzenesulfonyl)-4-nitrobenzenesulfonamido.

24. A compound of claim 1 wherein Y is 1-(2,4,6-triphenylpyridinium)tetrafluoroborate.

25. A compound of claim 1 wherein Y is diazo.

26. A compound of claim 1 selected from (2-methyl[1,1'-biphenyl]-3-yl)methyl 4-methylbenzenesulfonate, (2,4-dimethyl[1,1'-biphenyl]-3-yl)-methyl 4-bromobenzenesulfonate, (2,4,6-trifluoro[1,1'-biphenyl]-3-yl)methyl 4-chlorobenzenesulfonate, (2-methyl[1,1'-biphenyl]-3-yl)methyl methanesulfonate, (2,4-dimethyl[1,1'-biphenyl]-3-yl)methyl 2,2,2-trifluoroethanesulfonate, (2,4,6-trifluoro[1,1'-biphenyl]-3-yl)methyl trifluoromethanesulfonate, N-(2-methyl[1,1'-biphenyl]-3-yl)methyl-N-(4-methylbenzenesulfonyl)-4-methylbenzenesulfonamide, N-(2,4-dimethyl[1,1'-biphenyl]-3-yl)methyl-N-(4-nitrobenzenesulfonyl)-4-nitrobenzenesulfonamide, and 1-(2-methyl[1,1'-biphenyl]-3-yl)-methyl-2,4,6-triphenylpyridinium tetrafluoroborate.

27. A compound of claim 1 wherein Y is a pyridinium group.

* * * * *

UNITED STATES PATENT AND TRADEMARK OFFICE
CERTIFICATE OF CORRECTION

PATENT NO. : 4,668,792

DATED : May 26, 1987

INVENTOR(S) : Ernest L. Plummer

It is certified that error appears in the above-identified patent and that said Letters Patent is hereby corrected as shown below:

Column 8, line 1, "Colins", should read --Collins--; Column 8, line 49, "exemplfication" should read --exemplification"--.

Signed and Sealed this

Sixteenth Day of February, 1988

Attest:

DONALD J. QUIGG

Attesting Officer

Commissioner of Patents and Trademarks